(12) United States Patent
Guerin

(10) Patent No.: US 9,934,362 B2
(45) Date of Patent: Apr. 3, 2018

(54) GEOGRAPHICALLY SMOOTHED DEMOGRAPHIC CARTOGRAMS AND CARTOGRAM SERVER

(71) Applicant: OPENHEALTH COMPANY, Vannes (FR)

(72) Inventor: Patrick Guerin, Baden (FR)

(73) Assignee: OPENHEALTH COMPANY, Vannes (FR)

( * ) Notice: Subject to any disclaimer, the term of this patent is extended or adjusted under 35 U.S.C. 154(b) by 62 days.

(21) Appl. No.: 14/727,807

(22) Filed: Jun. 1, 2015

(65) Prior Publication Data

US 2016/0350507 A1    Dec. 1, 2016

(51) Int. Cl.
*G06T 11/20* (2006.01)
*G06F 19/00* (2018.01)
*G09B 29/00* (2006.01)

(52) U.S. Cl.
CPC ...... *G06F 19/3443* (2013.01); *G06F 19/3493* (2013.01); *G06T 11/206* (2013.01); *G09B 29/007* (2013.01)

(58) Field of Classification Search
None
See application file for complete search history.

(56) References Cited

U.S. PATENT DOCUMENTS

| | | |
|---|---|---|
| 6,853,386 B1 | 2/2005 | Keim et al. |
| 2015/0109338 A1* | 4/2015 | McKinnon ........ G06F 17/30244 345/633 |

OTHER PUBLICATIONS

Dorling, Daniel. "Visualizing changing social structure from a census." Environment and Planning A 27.3 (1995): 353-378.*
Hennig, Benjamin D. "Rediscovering the World: Map Transformations of Human and Physical Space." Springer Theses, Recognizing Outstanding Ph. D. Research (2013).*
Kapler, Thomas, and William Wright. "Geotime information visualization." Information Visualization 4.2 (2005): 136-146.*
Sabel, Clive E., and Anthony C. Gatrell. "Exploratory spatial data analysis of motor neurone disease in North West England: beyond the address at diagnosis." Geomed'97. Vieweg+ Teubner Verlag, 1998. 58-69.*
Stevenson, Mark, and I. V. A. B. S. EpiCentre. "Investigation of spatial patterns of animal disease." Advanced Analysis and Interpretation of Animal Health Data. Palmerston North, New Zealand (2009): 97.*
Tao, Manting. Using cartograms in disease mapping. Diss. The University of Sheffield, 2010.*

(Continued)

*Primary Examiner* — Ryan D McCulley
(74) *Attorney, Agent, or Firm* — Marshall, Gerstein & Borun LLP

(57) ABSTRACT

A contiguous cartogram is distorted proportionally to demographic data associated with geographical areas. The cartogram is associated with an underlying data set (such as health indication data or epidemiological data) that is geographically smoothed to avoid meshing and border effects, and shaded according to a predetermined shading scale. The cartogram may be stacked with other cartograms associated with underlying data sets collected at different times to form a chronological cartogram slideshow to illustrate changes in the underlying data set over time. The chronological cartogram slideshows may be transmitted from a map server via a communications interface to a requesting client.

29 Claims, 13 Drawing Sheets

(56) References Cited

OTHER PUBLICATIONS

Dorling et al., Worldmapper: the world as you've never seen it before, IEEE Trans. Visualization and Computer Graphics, 12(5):757-64 (2006).
Gansner et al., Visualizing graphs and clusters as maps, IEEE Computer Graphics and Applications, 30(6):54-66 (2010).
International Search Report and Written Opinion, International Application No. PCT/EP2016/062108 (dated Jun. 27, 2016).
Vellido et al., Cartogram visualization for nonlinear manifold learning models, J. Data Mining and Knowledge Discovery, 27(1):22-54 (2013).

* cited by examiner

GEOGRAPHICALLY SMOOTHED DEMOGRAPHIC CARTOGRAMS AND CARTOGRAM SERVER

FIELD OF THE INVENTION

The present invention relates generally to rendering visual geographical depictions of underlying statistical data, and, more particularly, to rendering demographically-based cartograms shaded to depict health or epidemiological data according to geographically smoothed data points based on the distorted distances between epidemiological or health data points on the cartogram surface rather than based on their Euclidean distances. The invention is also related to a map server for rendering and distributing cartograms including the creation and transmission of chronological series of cartograms.

BACKGROUND OF THE INVENTION

Cartographers often use Euclidean maps to illustrate the measurement of an underlying statistical or thematic variable across a geographical area, usually by shading the Euclidean map according to a shading scale corresponding to the measured value of the underlying variable. The shading scale is usually chosen as a progression from a light shade to a darker shade to show the level of the variable as it increases, and the shading is applied to regions of the map according to the average value of the thematic variable in that particular region. Maps shaded in this way are also known as choropleth maps, any they provide a way to visualize the measurement of a variable across a geographic area or to show the variability of the measurement within the region.

Choropleth maps are increasingly common in the field of communicating and interpreting epidemiological or health data due to the use of cartography software. However, it may be difficult for the viewer of a choropleth map to understand certain aspects of the presented data, especially under certain conditions relating to the distribution of the demographic variable. For example, if the demographic variable is not distributed evenly across the map, it is difficult to recognize the magnitude of the measurement and interpret the results because a large accumulation of data points could potentially be represented by a relatively small amount of space on the map. An example is a map illustrating a sampling of a per capita characteristic of persons over a country, such as household income, where low population areas contain far fewer individuals than urban areas, and thus a large fraction of the population will be represented on only a small fraction of the map surface, i.e., the higher density urban areas. The low population areas tend to dominate these maps when applied to typical real-world land use patterns. Viewers of Euclidean choropleths may fail to recognize this, especially if they are unfamiliar with the geography and density of the geographic area.

To provide a more intuitive presentation of thematic data over a geographical area, cartograms may be substituted for Euclidean choropleths. Cartograms are made by a technique wherein a demographic mapping variable substitutes for land area as normally shown on an Euclidean map. A cartogram distorts the surface of the Euclidean map to depict a zone's area on the map as proportional to the level of the demographic variable contained therein. Cartograms therefore do not depict actual geographic space. Cartogram zones may include anything that exists in geographic space such as a country, state, city, county, borough, town, river, mountain range, etc. Common types of cartograms include distance cartograms, which are distorted to show travel time between points, and value-by-area cartograms, which are distorted to show the prevalence of a characteristic that varies according to location on a map, usually a demographic characteristic such as population, votes for a candidate, number of patents filed, number of automobiles owned, gross domestic product, educational level, etc. When a value-by-area cartogram is based on population, it is often termed an isodemographic map. In this way, an isodemographic map would illustrate the relative sizes of the populations of real-world areas by scaling the area allotted to each according to its population rather than to its physical geographical area in the conventional manner. For example, if a region accounts for 20% of the population of a country, it will occupy 20% of the surface area on an isodemographic cartogram of that country.

Euclidean maps may be distorted to create cartograms according to a number of known algorithms that may differ in their effects on the map's continuity, shape preservation, orientation, and topology preservation relative to the Euclidean map. For example, a cartogram distortion algorithm that forces neighboring map features to maintain their borders regardless of the distorted size of the features is known as a contiguous cartogram. In a contiguous cartogram, the topology between objects is maintained, but, as a group, the objects may lose their shape, giving the cartogram a "pinched" appearance, depending on the amount of distortion. Contiguous cartograms may render the depicted geographical area unrecognizable to a viewer if there are physical geographical areas that have little or no measurement of the underlying thematic variable. For example, contiguous isodemographic cartograms appear to omit low population areas that occupy large amounts of geographic space, such as a desert or mountain region.

A non-contiguous cartogram, on the other hand, does maintain connectivity between adjacent features, but instead allows the features to grow or shrink in size and still maintain their familiar shape. Non-contiguous cartograms may, instead of enlarging or shrinking map objects, replace them with objects of a uniform shape such as, for example, a circle or vertical bar. Shapes in a non-contiguous cartogram often do not overlap, but rather are rearranged so that the full area of each shape can be seen.

Each of these existing cartogram rendering methods provides a different visual appearance of the data, and may be more or less suitable for communicating and interpreting underlying data depending on the data's distribution. These cartogram rendering methods, however, suffer from a drawback that impairs the presentation of the underlying data. In these cartograms, shaded zones are based on administrative boundaries representing arbitrary borders or borders that do not align with population patterns such as towns, boroughs, counties, cities, regions, states, territories, or other ad-hoc groupings such as those based on industry criteria. These zones may introduce abrupt transitions in the shading pattern of the map due to issues such as meshing or border effects. Meshing effects are due to the variations in size of geographical zones, especially towns and cities; border effects result in variables that can seem to have major differences between two neighboring zones even though the variables likely change smoothly and continuously over the area in reality. Adjusting the size of zones does not provide a satisfactory solution to the problem. On one hand, if the zones are chosen to be small units to obtain good geographical accuracy and avoid the meshing and border effects, the map will take on an inlaid effect that will make it difficult for the viewer to read and interpret. On the other hand, if the zones are enlarged, then the map will be easy for the viewer to read, but will diminish accuracy and a reduce resolution of information conveyed to the viewer.

SUMMARY OF THE INVENTION

The cartograms disclosed herein are demographically-based shaded cartograms with geographically smoothed data points for presenting thematic data with an improved visual expression, minimizing distortions introduced by administrative boundaries and data distribution. Embodiments include a cartogram server for rendering and distributing the cartograms including creation and transmission of chronological series of the cartograms.

Aspects of the health indication cartograms may include: that it is a contiguous cartogram; the cartogram is tessellated into regular hexagons and distorted such that each hexagon's area represents an equal amount of human population or other demographic characteristic; there are geographical collection units reporting an epidemiological or health indication value and, optionally, a demographic value; the cartogram is further tessellated into regular hexagon geographical representation units; the health indication or epidemiological values are geographically smoothed according to a weighting function that depends on a predetermined distance of interest; and the cartogram is shaded according to a predetermined shading scale based on the geographically smoothed values.

The present embodiments as disclosed herein may enable an organization with access to epidemiological or health indication data across a geographical region such as, for example, a country, state, or territory, to render a health indication cartogram or a series of health indication cartograms to illustrate an epidemiological state or the progression of the epidemiological state over time across the geographical region. The present embodiments may allow for flexibility in rendering cartograms across geographical regions with varying population density patterns and variations in the distribution of the available geographical collection units. The present embodiments may also provide for a cartogram map server suitable for transmitting a plurality of health indication cartograms in response to a client request for a geographical region and an associated health indication or epidemiological variable.

In one aspect, a method of rendering health indication cartograms may be provided. The method may include retrieving a geographic map projected in a Euclidean plane; tessellating the geographic map projected in a Euclidean plane into a plurality of cartogram tiles; receiving demographic data associated with each of the plurality of cartogram tiles indicating a demographic characteristic of the geographic area represented by each cartogram tile; proportionally distorting the area of each of the plurality of cartogram tiles to form a demographically-based cartogram such that the borders of each cartogram tile remain contiguous to its neighboring cartogram tiles and the surface of each cartogram tile is proportional to the demographic characteristic of the geographic area represented by the cartogram tile; receiving data associated with each of a plurality of geographical collection units, each geographical collection unit comprising a health indicator value and a geographic location coordinate; tessellating the demographically-based cartogram into a plurality of geographical representation units, each corresponding to a geographical area and each having a health indicator value associated therewith; geographically smoothing the heath indicator value of each geographical representation unit according to a weighting function applied to each geographical collection unit located in the geographic area corresponding to the geographical representation unit; and rendering a health indication cartogram wherein each geographical representation unit is shaded according to a predetermined shading scale based on the geographically smoothed health indicator value of the geographical representation unit.

In another aspect, a health indication cartogram server may be provided. The server may include a program memory; a map database containing a plurality of contiguous demographically-based cartograms representing a geographical area, each tessellated into a plurality of cartogram tiles, each cartogram tile representing equal total population, and each demographically-based cartogram further tessellated into a plurality of geographical representation units, each geographical representation unit having a health indicator or epidemiological value associated therewith; and a geographical collection unit database containing geographical collection units located in the geographical area, each geographical collection unit including a health indicator or epidemiological value, a geographical location, and a collection date stamp. The program memory may be further configured to receive geographical collection units from the geographical collection unit database with collection date stamps within a predetermined range; geographically smooth the health indicator or epidemiological values of each geographical representation unit according to a weighting function applied to each geographical collection unit located in the area represented by the geographical representation unit; render a plurality of health indication cartograms, each containing only geographical representation units with a collection date stamp within a predetermined range; and transmit the plurality of health indication cartograms to a client in response to a client request via the communications interface for display in chronological order according to the collection date stamps.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, whenever possible, the following description refers to the reference numerals included in the following figures, in which features depicted in multiple figures are designated with consistent reference numerals.

DETAILED DESCRIPTION OF THE PREFERRED EMBODIMENTS

The present invention is described in connection with preferred embodiments. The demographic cartograms are an intuitive solution for researchers and cartographers to display data, or sets of data, associated with a geographical area. The cartograms may provide visibility into the effects of any measurable variable across a geographical area, and will assist viewers to evaluate the implications of the measured variable without interference from obfuscations typical on choropleths and cartograms including meshing and border effects by geographically smoothing the shaded data points.

In one aspect, multiple cartograms may be stacked into a chronological slideshow to animate changes of the underlying variable over time. The present embodiments recognize the value to researchers, public health officials, observers, citizens, and other interested parties to understand the changes to an underlying mapping variable over time. For instance, if the measured variable is incidence of lice infection, a communicable condition, the chronological stack of health indication cartograms will reveal features such as local hotspots, patterns of infection, and potential dangers to dense population centers or other vulnerable areas. In one embodiment, the chronological slideshow of cartograms may be transmitted via a communications device in response to a request from a client. The cartogram server and chronological stack are improvements to the field of cartography because they enable a new presentation of demographically-based data to convey information not available in conventional maps.

I. Exemplary Cartograms

Use of the cartogram is especially suited to human population epidemiology because the visual appearance of each unit of the cartogram's area is proportional to the human population inside that area, rather than simply showing the geographical area's surface as with traditional Euclidean maps. Human population epidemiology cartograms are particularly suited to illustrations of correlations between population distribution and the propagation of a contagious disease among individuals in that population.

Figure 1A:
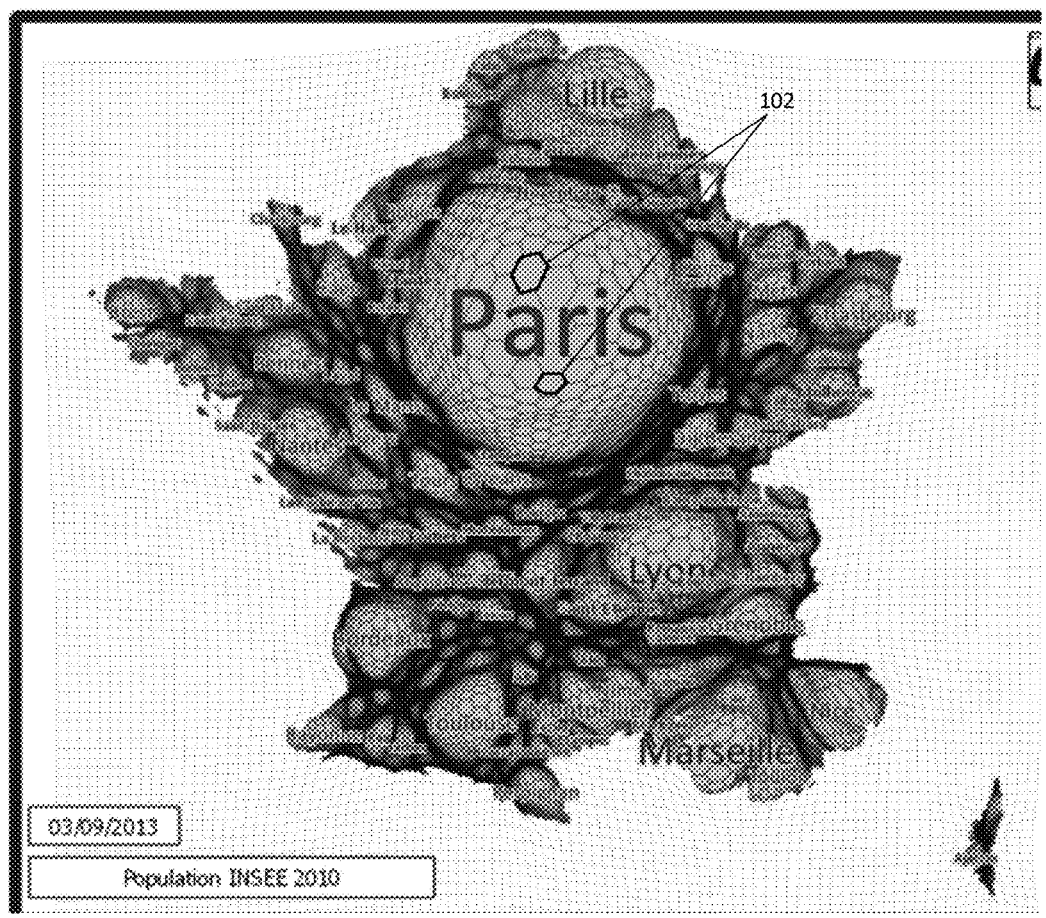
FIGS. 1A and 1B are isodemographic cartograms of France and North America, respectively.
Figure 1B:
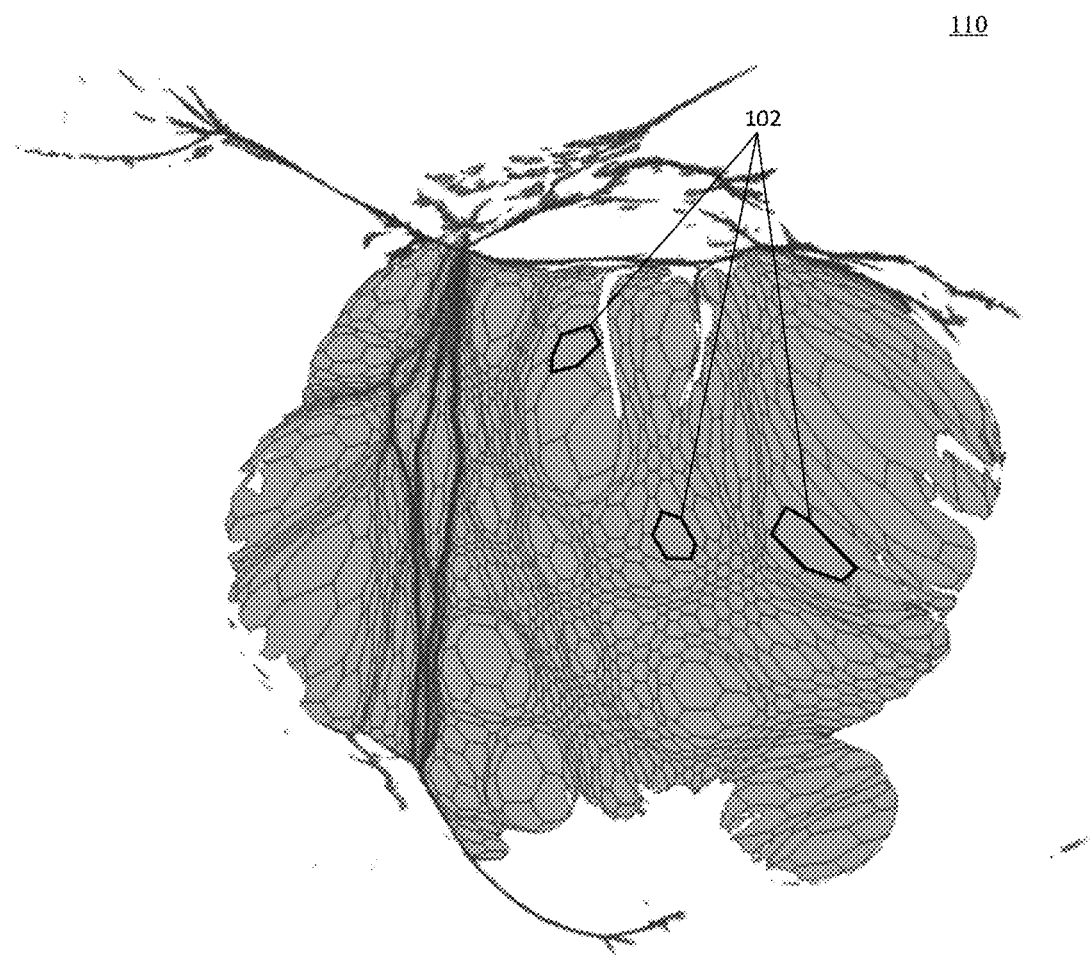

FIG. 1A illustrates an exemplary cartogram 100 based on a data set containing the 2010 population of France, as provided by the French National Institute of Statistics and Economic Studies of France. Cartogram 100 was formed by tessellating the provided Euclidean map into 71,304 kilometer hexagonal tiles 102, the sides of each hexagonal tile 102 measuring one kilometer in length, then proportionally distorting the area of the hexagonal tile 102 such that the borders remain contiguous to its neighboring cartogram tiles 102 and the surface of each is proportional to the population according to the provided 2010 population data set. The contiguous feature of this cartogram and the choice of the hexagon as the shape of the cartogram tiles produce a 3D relief effect because heavily populated areas appear as "bubbles" on the cartogram. FIG. 1B illustrates another exemplary cartogram 110 of North America, also tessellated into hexagonal cartogram tiles 102.

II. Geographical Collection Units

Figure 2:
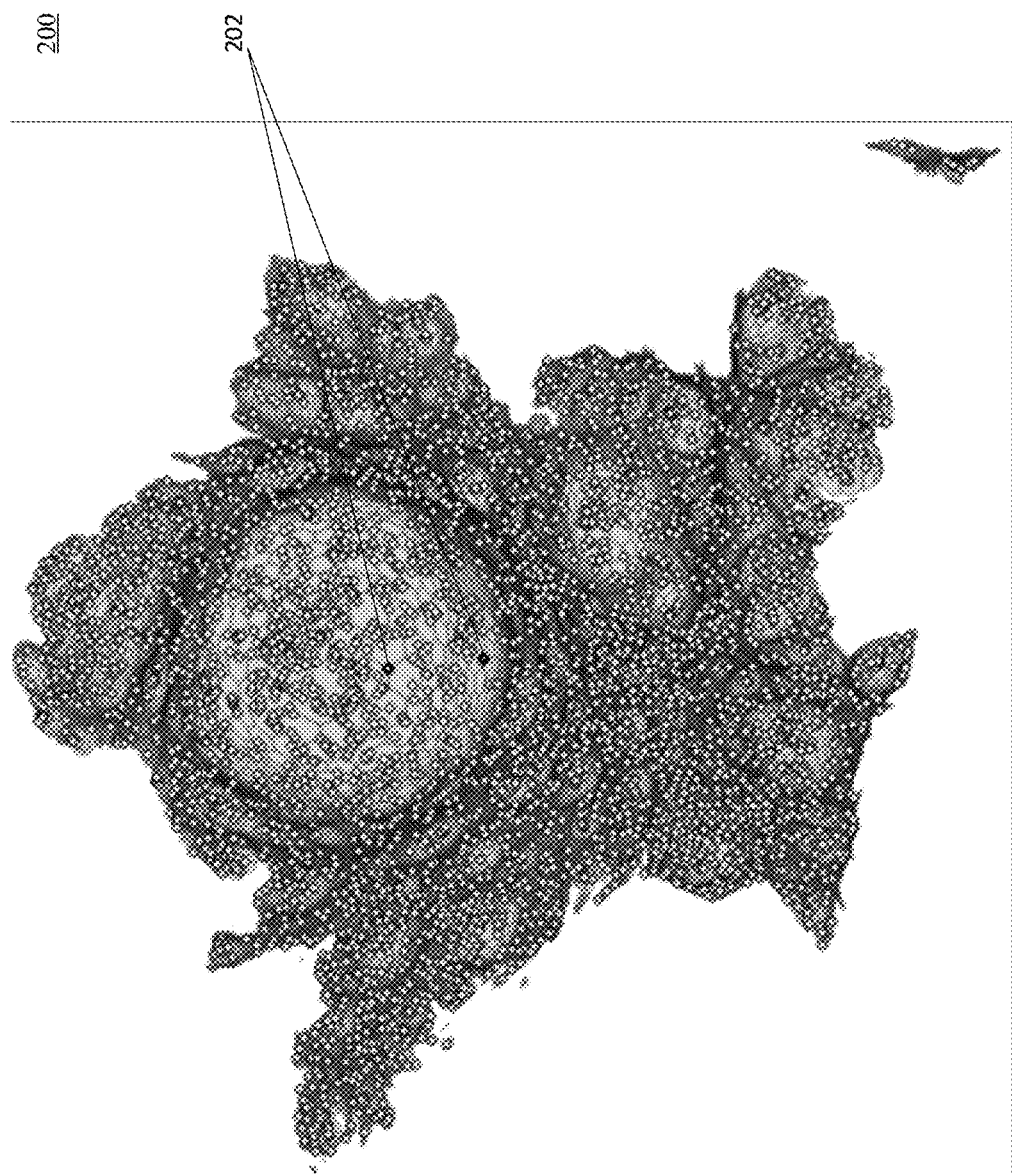
FIG. 2 illustrates geographical collection units on an isodemographic cartogram of France.

Geographical collection units are the points of data collection forming a data set to be illustrated by a cartogram in accordance with embodiments of the invention as disclosed herein. In an example, the geographical collection units are pharmacies in a real-time reporting network located in towns for which population data is known. The pharmacies supply data relating to the variable to be studied, and the towns supply corresponding population or other relied-upon demographic data. For example, the pharmacies may report the number of prescription medications renewed for the treatment of gastroenteritis. FIG. 2 illustrates a cartogram 200 with overlaid geographical units 202. The geographical location of the geographical collection units is determined by their real-world location, and their associated demographic information is derived from the demographic variables of the towns in which they are located. In an example, if a geographical collection unit is located in a town of 20,000 residents, and it is a pharmacy that has dispensed 100 doses of the medication of interest, e.g., medication relating to gastroenteritis, the geographical collection unit would be assigned a value of 50, representing the dispensations per 10,000 residents. Any suitable scale may be used to select the values of the geographical collection units for ease of presentation.

III. Geographical Smoothing

The invention, in some embodiments, counters effects that cause difficulty to the viewer or loss of geographical accuracy, such as meshing and border effects, by the technique of geographical smoothing. According to the technique of geographical smoothing, the values observed at a given point, or in a zone, are replaced by a weighted average depending on the values observed around it. Weightings decrease inversely to distance until they vanish at a distance termed the "distance of interest." The result is a weighting of a measurement value according to the average observations in the neighborhood around the weighted value. Geographical smoothing further shows data at a level that is different from the level of data collection, shows the collected data at different geographical levels from the geographical collection units. Geographical smoothing provides an additional advantage because it obscures the identity of the geographical collection units, as may be required pursuant to data privacy laws or regulations. On a geographically smoothed cartogram, the geographical collection units cannot be identified or linked to specific medical data pertaining to individuals or groups.

One suitable weighting function for geographically smoothing is a non-parametric statistical function known as the biweight function. An expression of the biweight function is shown below in Formula 1:

$$p = \left[1 - \left(\frac{d}{D}\right)^2\right]^2$$

avec $d < D$

It is believed that the choice of weighting function itself does not bear significantly on the final result of the demographically-based cartogram. Another suitable weighting function is the Gaussian function. It is advantageous to choose a weighting function that facilitates the calculations over a potentially large number of geographical collection units. Compared to a Gaussian function, the biweight function has the advantage of making the calculations simpler. Regardless of choice of weighting function, the weighting function parameter with the greatest influence on the final result is the distance of interest. As examined below in Section V, adjustments to the distance of interest constant in the weighting function affect the appearance of the final health indication cartogram by varying the data from a highly granular appearance for a lower distance of interest to a more smoothed, but less accurate, appearance for a higher distance of interest.

Figure 3:
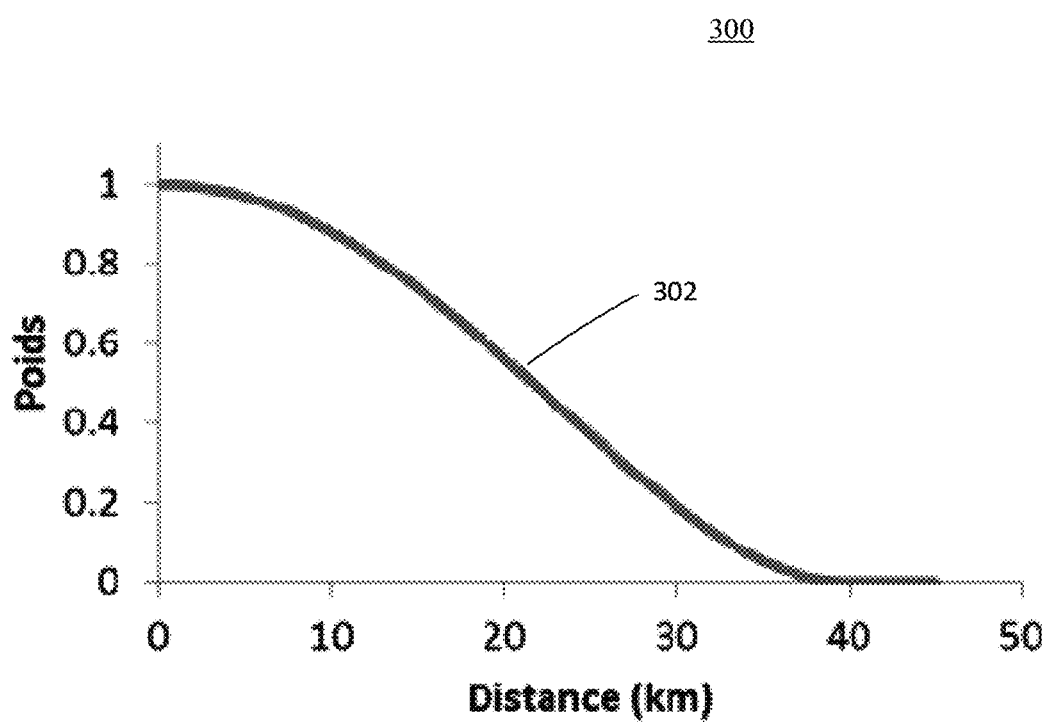
FIG. 3 is graph of an exemplary biweight function.

FIG. 3 is a graph 300 of an exemplary biweight function. The weighting value 302 is shown on the y-axis, and ranges from a maximum of 1 to a minimum of 0. The weighting value of 1 is obtained when the distance between the smoothed point and a neighboring point is 0. The weighting value of 0 is obtained when the distance between the smoothed point and a neighboring point is greater than the predetermined distance of interest. In the example of FIG. 3, the distance from the geographically smoothed point to the neighboring point is shown on the x-axis, and the predetermined distance of interest has been chosen to be 40 kilometers. Other suitable predetermined values for the distance of interest may also be chosen, and examined in more detail below in Section V.

It is important that the geographical smoothing calculation be carried out on quantity variables that can be added, for example, number of cases of a diagnosis or intensity of an epidemiological health measurement. The geographical smoothing must never be carried out using ratios. On the other hand, the results are more often mapped in the form of ratios of two (or more) smoothed variables. This makes it possible to show a result that is easy to understand, whereas it is difficult to characterize the unit for the smoothed variables.

IV. Geographical Representation Units

Figure 4:
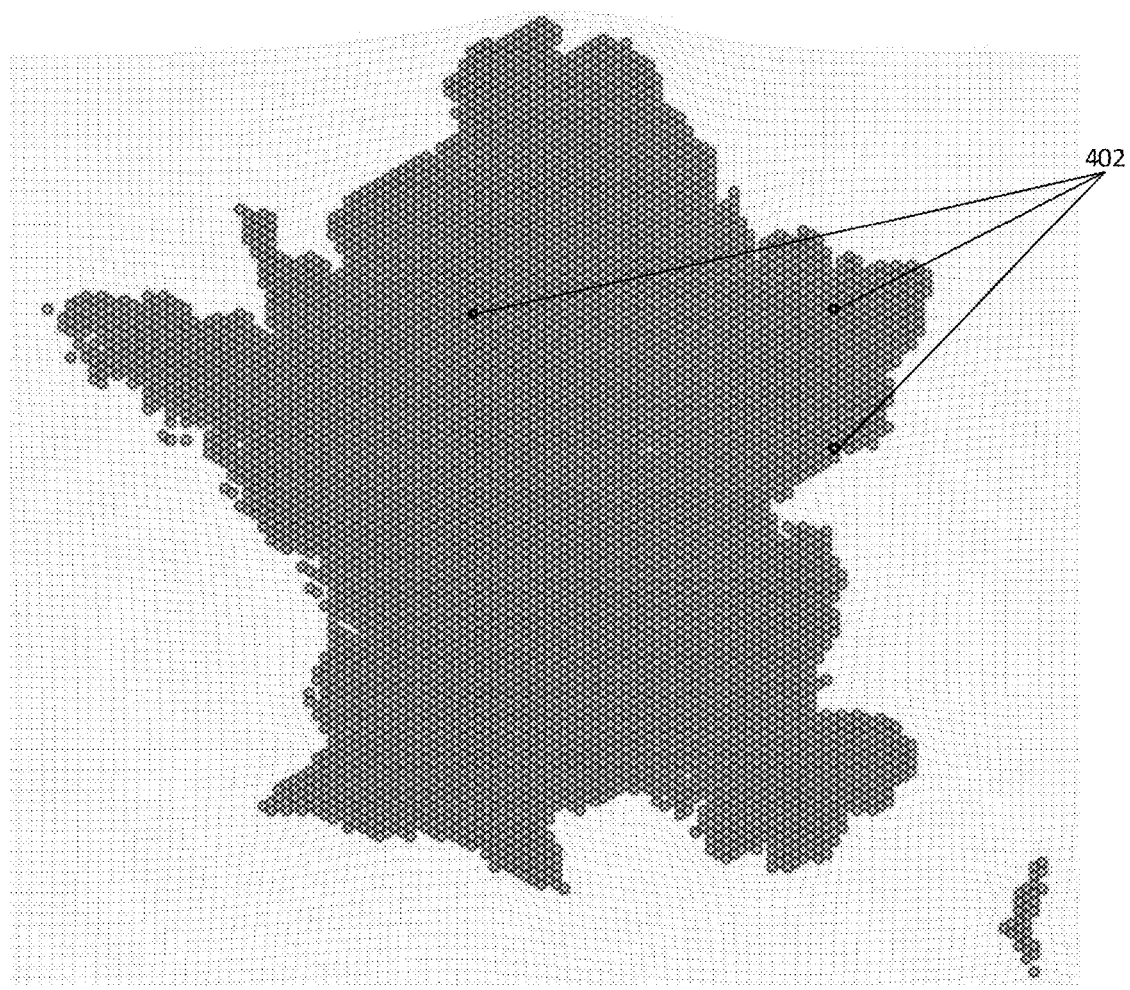
FIG. 4 is an isodemographic cartogram of France tessellated into regular geographical representation units.

FIG. 4 illustrates a cartogram tessellated into 6,311 hexagons with 10 kilometer sides to form geographical representation units 402. A geographically smoothed value is calculated for each geographical representation unit according to a suitable weighting function based on the geographical collection units located in the geographical territory covered by the geographical representation unit. The distance variable employed in the weighting function calculation, however, is not the distance between geographical collection units as measured in Euclidean space. Rather, it is the distance between geographical collection units after taking into account the distortion of the cartogram. In other words, distorting the Euclidean map to make a cartogram changes the distance between geographical collection units. The distortion may be carried out according to any of a known number of algorithms for creating cartograms. The distance between geographical collection units may be calculated according to a Euclidean distance function, an arc length, or other methods of calculating distance, either in a straight line or along a curved surface. The result is that the population of the area represented by each geographical representation unit is identical. A particular advantage of this approach is that it offers the same geographical estimation accuracy at all points on the territory, regardless of the population density.

V. Choice of Distance of Interest

Figure 5A:
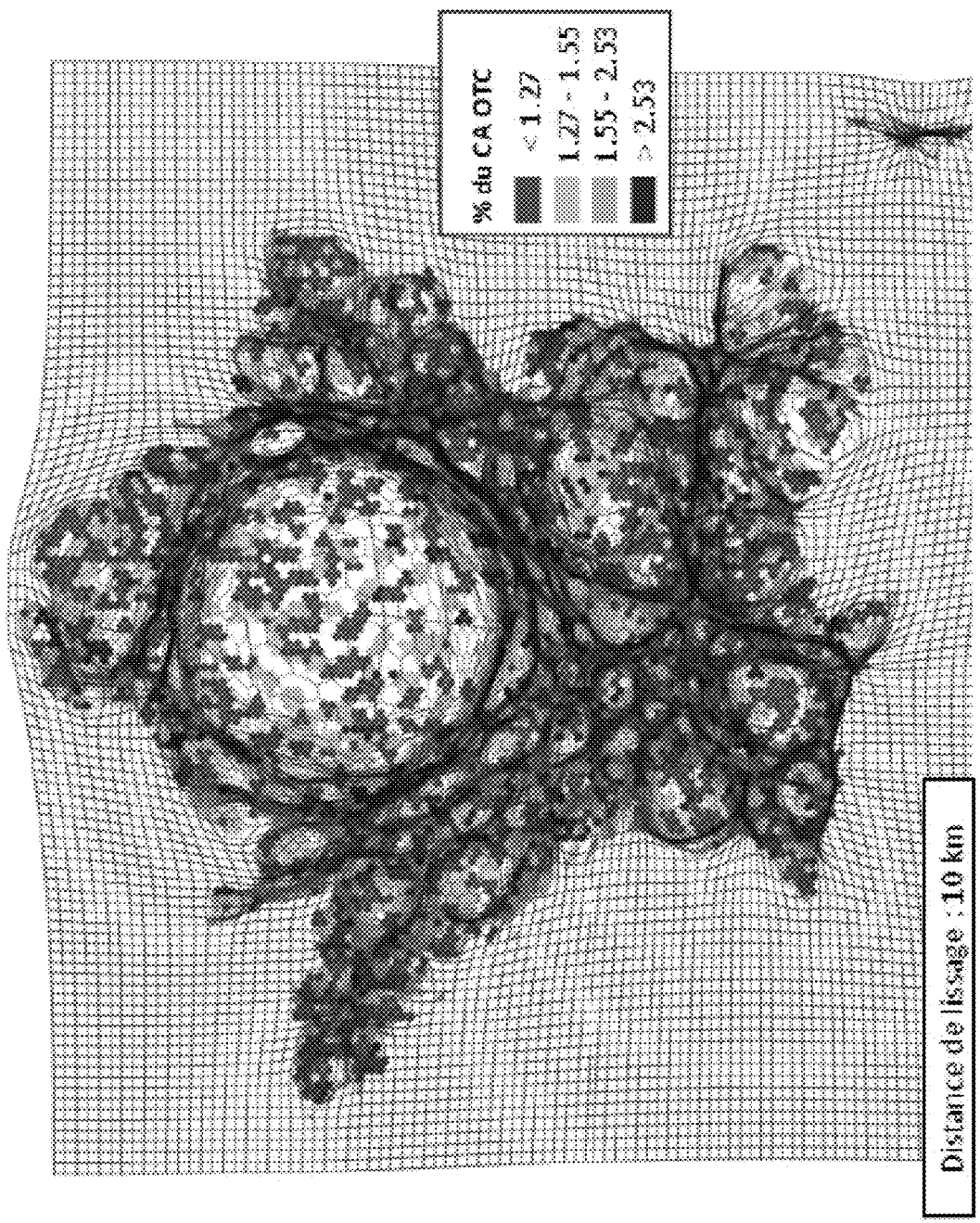
FIGS. 5A-5C illustrate the influence of adjusting the smoothing distance of interest constant in the weighting function on cartogram appearance.
Figure 5B:
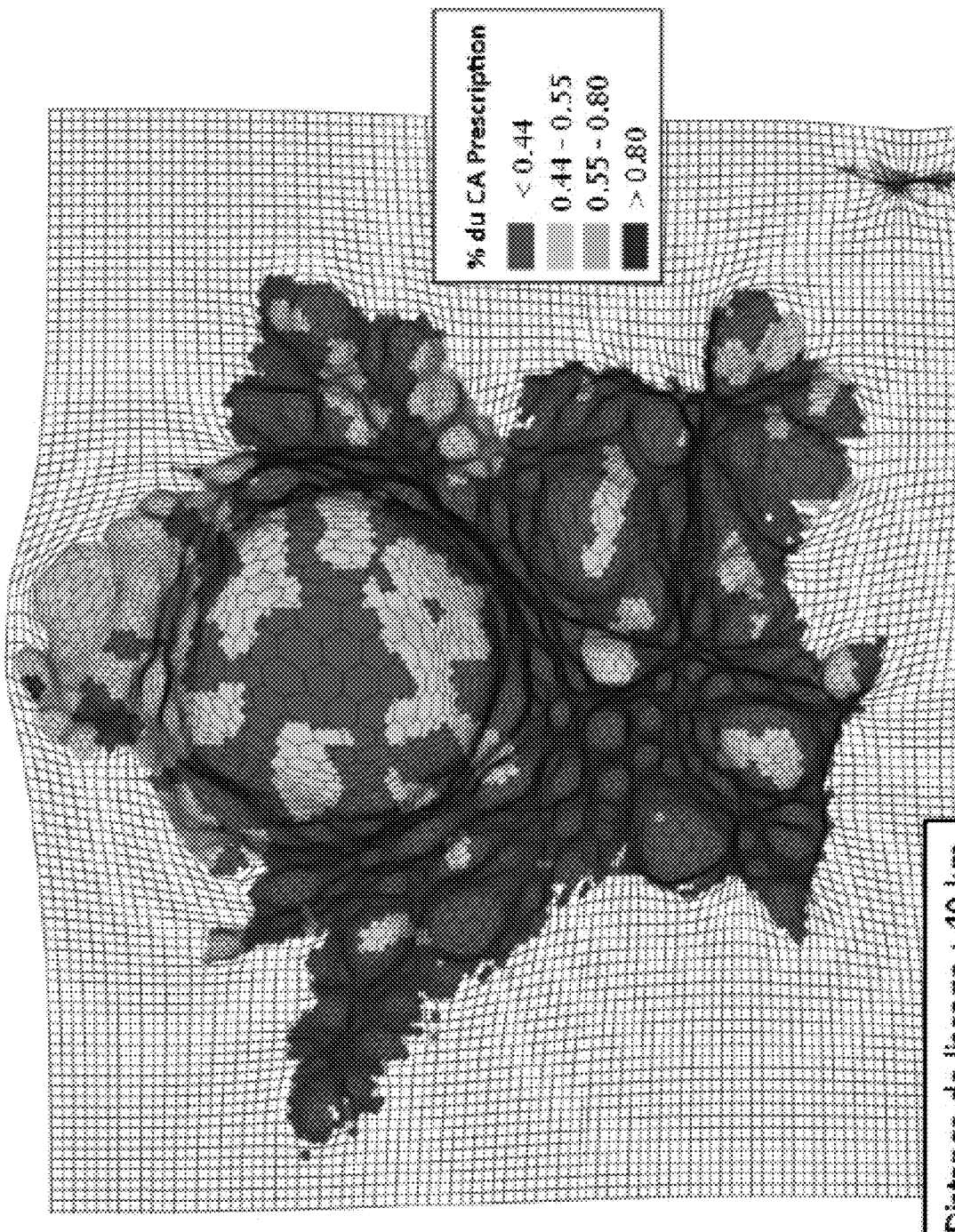
Figure 5C:
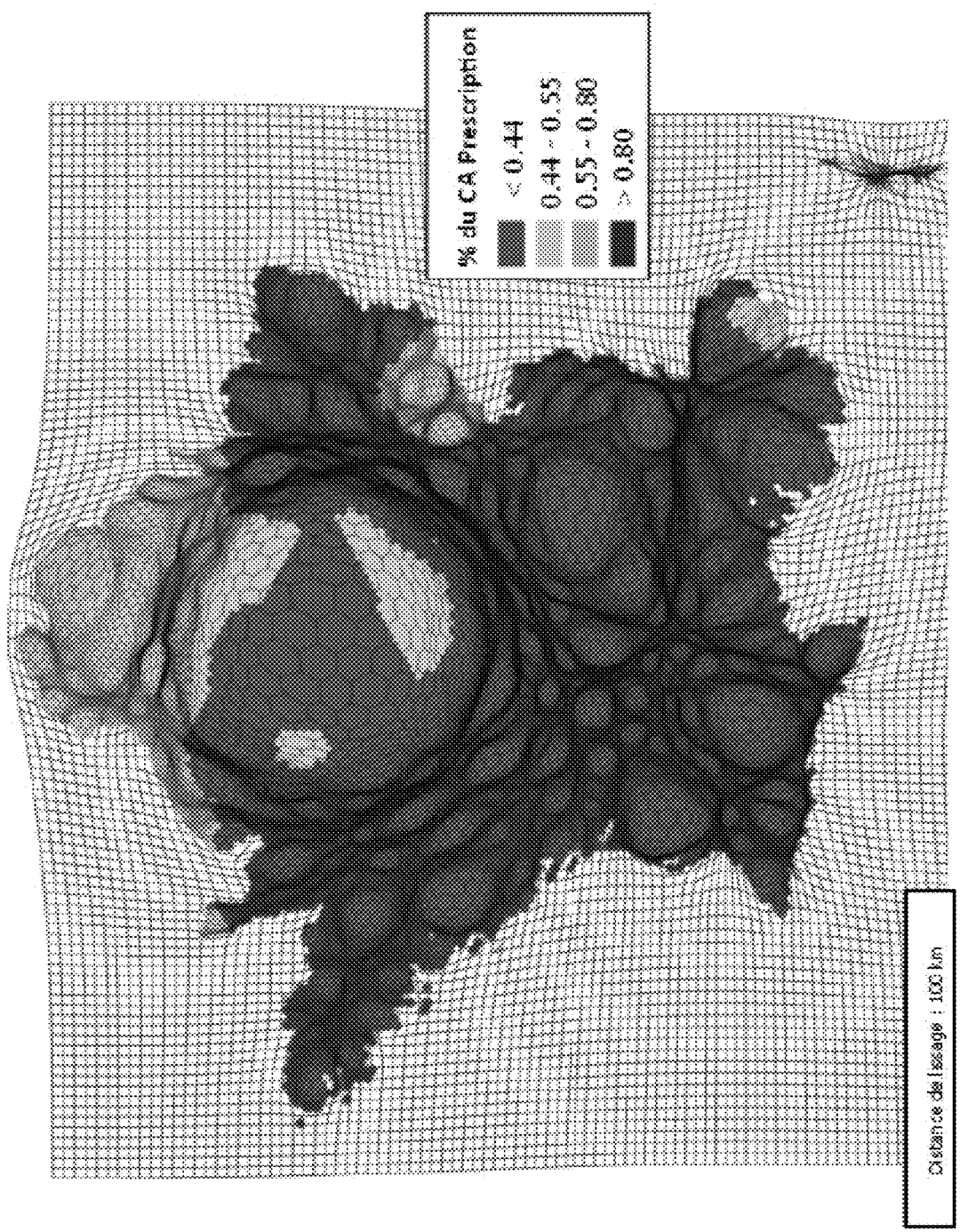

As referenced above, the choice of the distance of interest in the weighting function has a large effect on the visual appearance of the resulting health indication cartogram. The higher the distance of interest, the more colors are homogenized on the cartogram. Choosing a lower distance of interest will smooth the data points to a lesser extent, which may introduce an undesirable inlaid effect. FIGS. 5A-5C illustrate health indication cartograms generated according to an embodiment of the invention using the same set of geographical collection unit data, but with distance of interest choices of 10, 40, and 100 kilometers, respectively. For example, FIG. 5A, with a distance of interest choice of 40 kilometers, shows several localized high incidence zones in the South of Paris that do not appear on FIGS. 5B and 5C. The presence of these zones may be due to a better sensitivity in that it is highlighting an actual phenomena or to a lesser specificity in that the zones are an artifact caused by a network specificity (or perhaps a very local issue). In the absence of local reference data, it may not be possible to determine which is the cause of the high incidence zones. It is understood to be desirable in most cases to choose a larger distance of interest for most data sets to concentrate on regional phenomena rather than a shorter distance of interest concentrating on more local phenomena, an approach that is more prone to "false alarms."

VI. Exemplary Method

Figure 6:
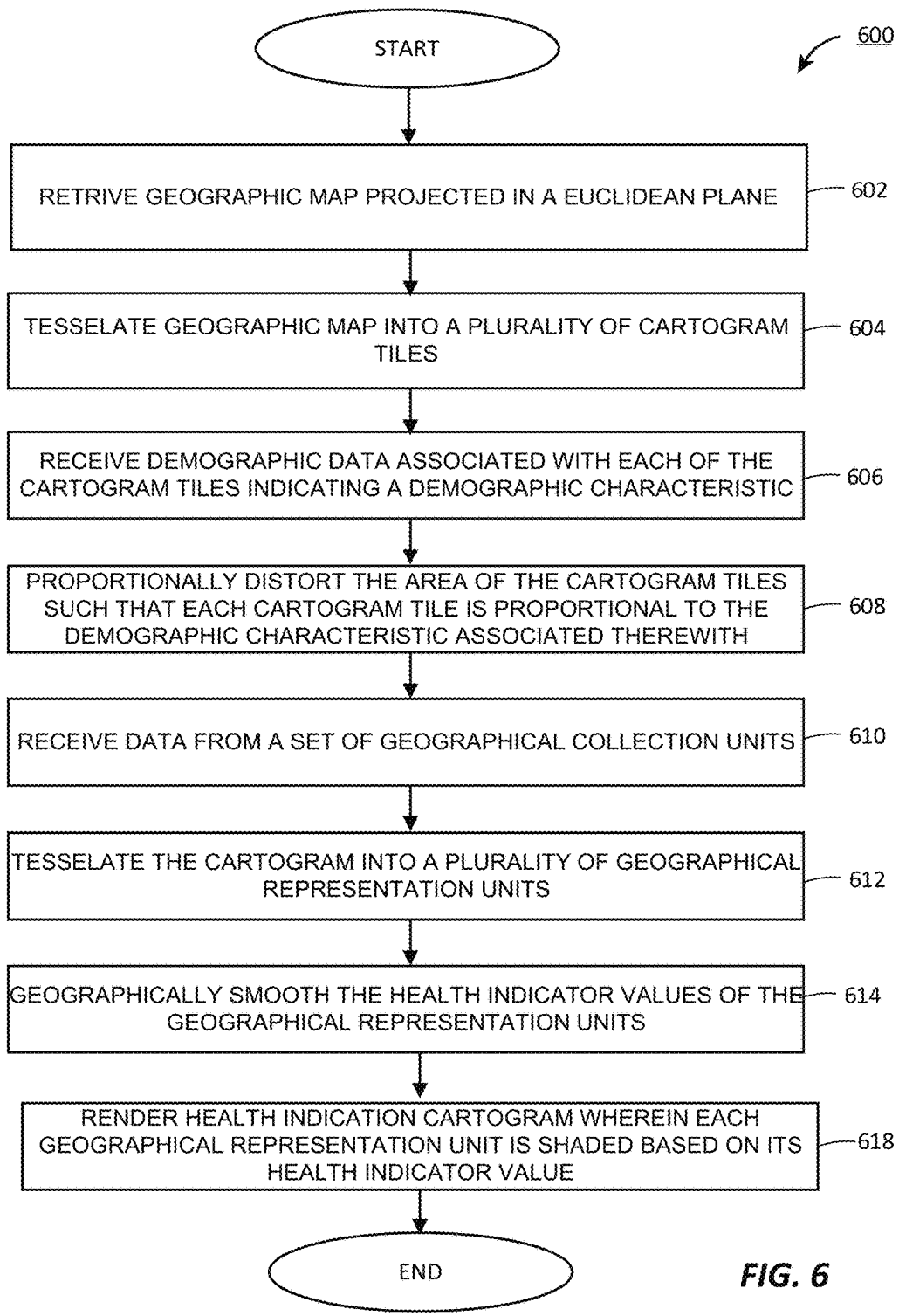
FIG. 6 is an exemplary flowchart for generating health indication cartograms.

An exemplary method 600 according to some embodiments is shown in FIG. 6. Receipt of a geographic map projected in a Euclidean plane may occur at step 602. Receipt of a geographic map in a Euclidean plane may be done in a variety of ways. In one embodiment, the geographic map in a Euclidean plane may be an input to map database 804 as explained in more detail below with reference to FIG. 8. In other embodiments, the geographic map in a Euclidean plane may be retrieved from a remote server such as via the communications interface of hardware server 820 via network 822.

At step 604, the geographic map is tessellated into a plurality of cartogram tiles. The tessellation may be a regular, semi-regular, or other tessellation of the map. In one embodiment, the tessellation is into a plurality of cartogram tiles in the shape of hexagons. Step 606 is receipt of demographic data associated with each of the plurality of cartogram tiles indicating a demographic characteristic. The demographic data may be any type of demographic data or data relating to demographic characteristics including population, economic data, household income levels, educational levels, votes for a political candidate, security, crimes, ethnicity, age, and any other measurable demographic characteristics. The demographic data may be further processed or refined such as in the example of a per capita, average, mean, median, or mode calculation before it is associated with a cartogram tile.

At step 608, the area of each cartogram tile is distorted such that each tile is proportional in area to the demographic characteristic expressed by the demographic data received in step 606. In one embodiment, the tiles remain contiguous to neighboring tiles. At step 610, the values are received from a plurality of geographical collection units. The geographical collection units may be any source of measurement of the demographic data. For example, the geographical collection units may be health care facilities that record and report a relevant measurement such as amount or number of medication dispensed. The measurement at the geographical collection units could also be an aggregate or normalized value depending on another value such as the population of an administrative unit in which the geographical collection unit is located. For instance, if the geographical collection units are a network of pharmacies, the reported value may be the number of times a prescription for a drug of interest was renewed at the pharmacies in a town divided by the total population of the town to produce a per capita incidence of prescription renewal for that geographical collection unit.

At step 612, the cartogram is again tessellated into a plurality of geographical representation units. In one embodiment, the tessellation is into a plurality of cartogram tiles in the shape of hexagons. Each geographical representation unit may then be assigned a value according to the values of the geographical collection units contained therein. At step 614, the values of the geographical representation units are geographically smoothed according to a weighting function depending on a distance of interest and a distance to other values as measured along the distorted surface of the cartogram rather than in Euclidean space. At step 618, the cartogram may be rendered wherein each geographical representation unit is shaded based on its geographically smoothed health indicator value.

VII. Exemplary Cartogram Map Server and Method

Figure 7:
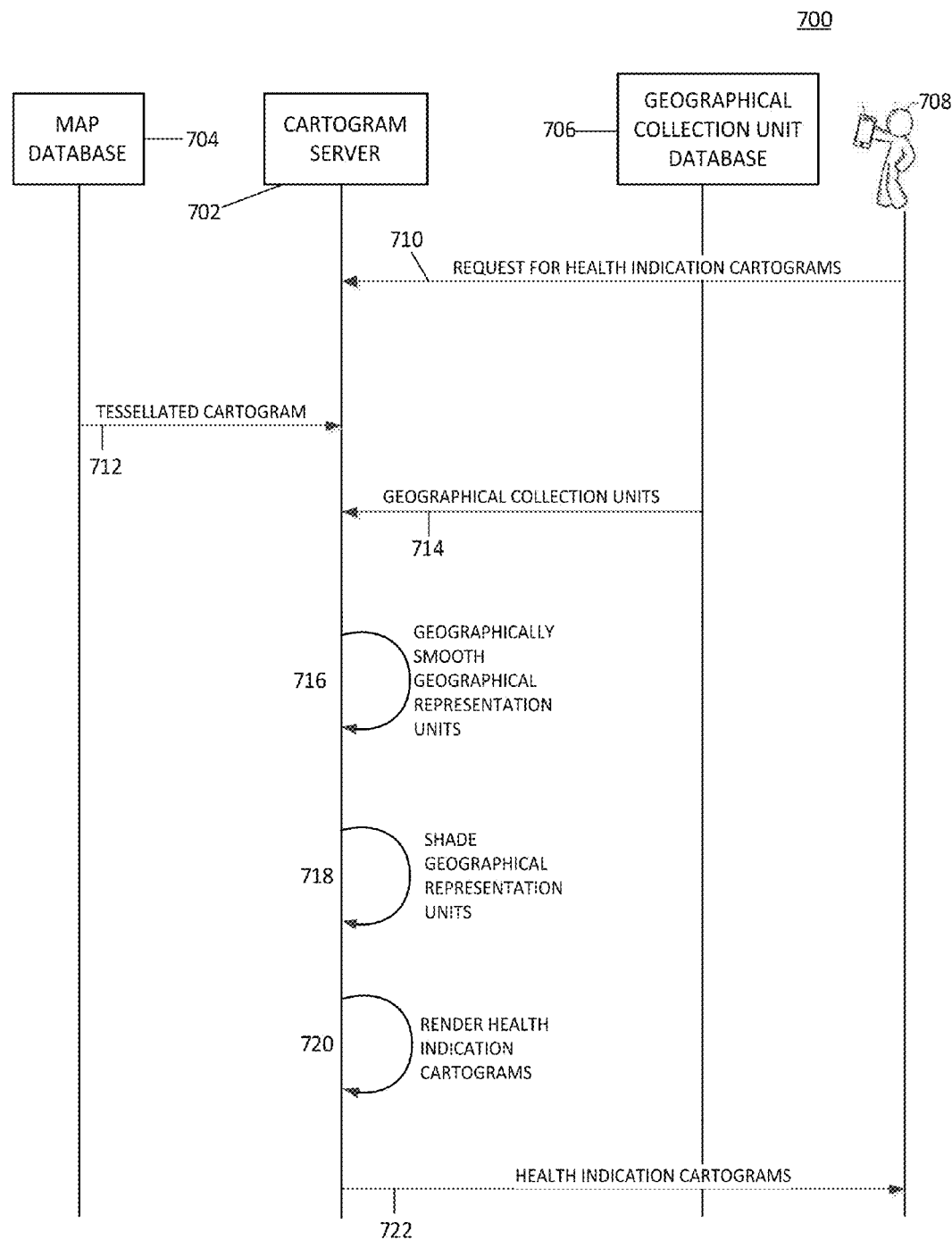
FIG. 7 is a signal diagram for operating an exemplary health indication cartogram map server.

FIG. 7 is an exemplary signal diagram 700 illustrating the operation of the cartogram server according to an embodiment of the present inventive concept. More specifically, at least one embodiment of 700 may control a health indication cartogram server including a map database, a geographical collection unit database, a communications interface, one or more processors, and a program memory storing instructions. The instructions are executable to cause cartogram server 702 to request health indication cartograms at step 710 from map database 704. At step 712, cartogram server 702 further receives one or more tessellated cartograms from map database at step 712. Cartogram server 702 may alternatively receive a Euclidean map from map database 704 and perform the tessellation locally. Cartogram server 702 further retrieves geographical collection unit data set at step 714 from geographical collection unit database 706. At step 716 cartogram server 702 geographically smooth values of each geographical representation units according to a weighting function applied to each geographical collection unit located in the geographical representation unit. Cartogram server 702 shades geographical representation units at step 718 according to a predetermined shading scale based on the geographically smoothed indicator values of the geographical representation unit. At step 720, cartogram server 702 renders a plurality of health indication cartograms, wherein each health indication cartogram represents data collected on the same day as reflected by the date stamp associated with the data. At step 722, transmitting the plurality of health indication cartograms to a client 708 in response to a client request via the communications interface for display in chronological order to client 708 according to the date collection stamps.

Figure 8:
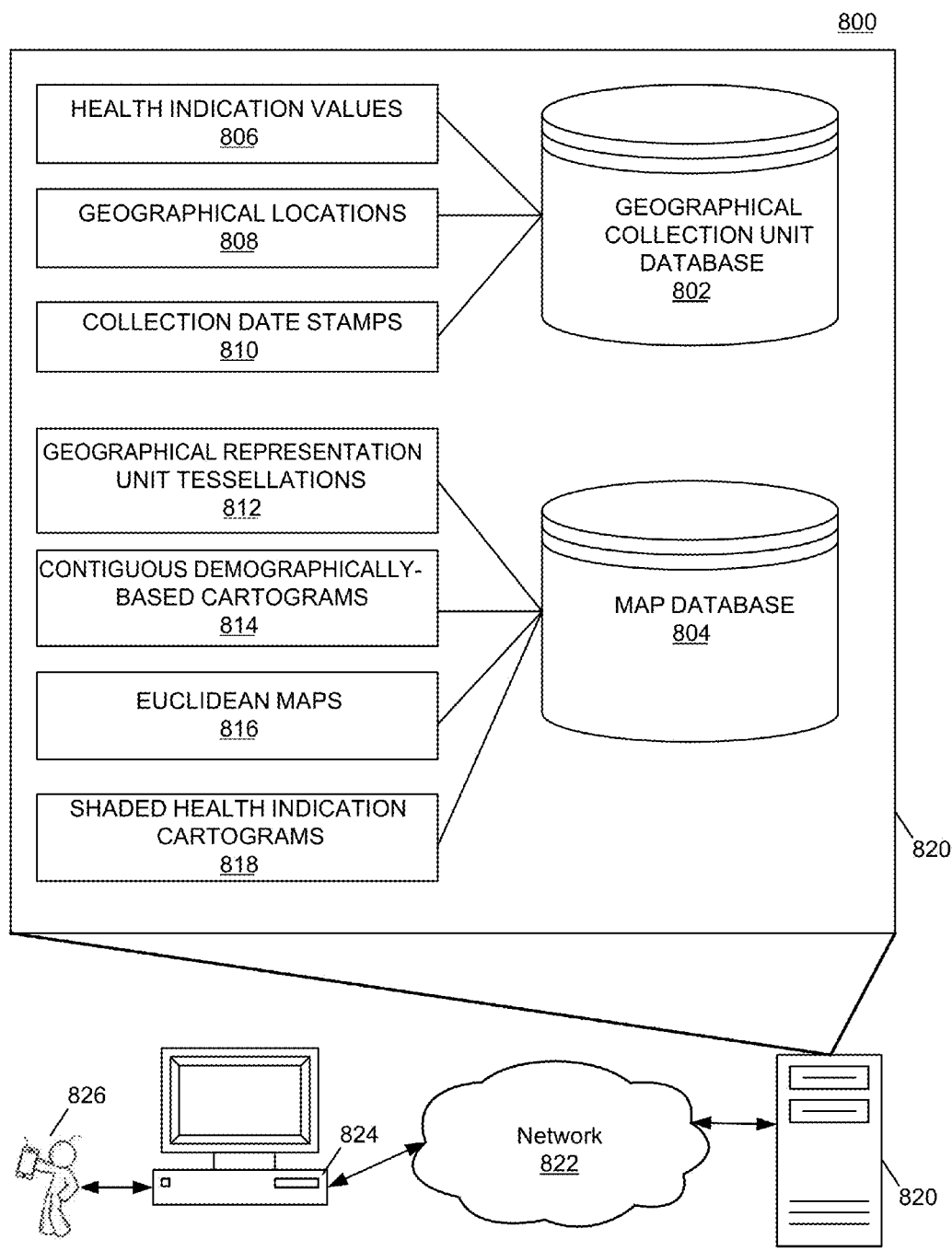
FIG. 8 depicts an exemplary environment including components and entities associated with generating cartograms and transmitting the cartograms from a map server to a requesting client.
Figure 9A:
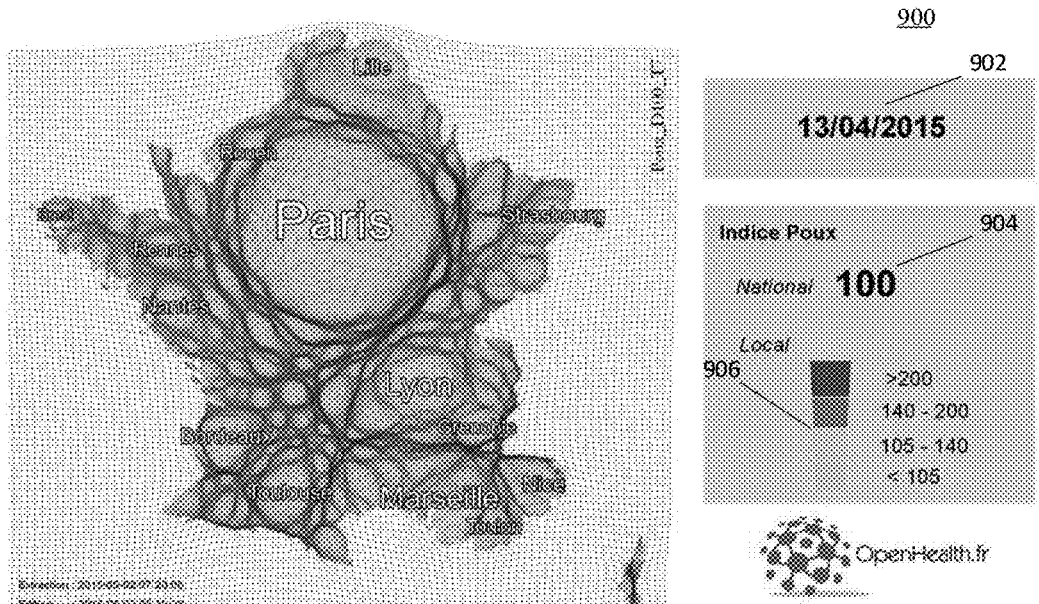
FIGS. 9A-9D are an exemplary output of four chronological isodemographic health indication cartograms transmitted from a health indication cartogram server.
Figure 9B:
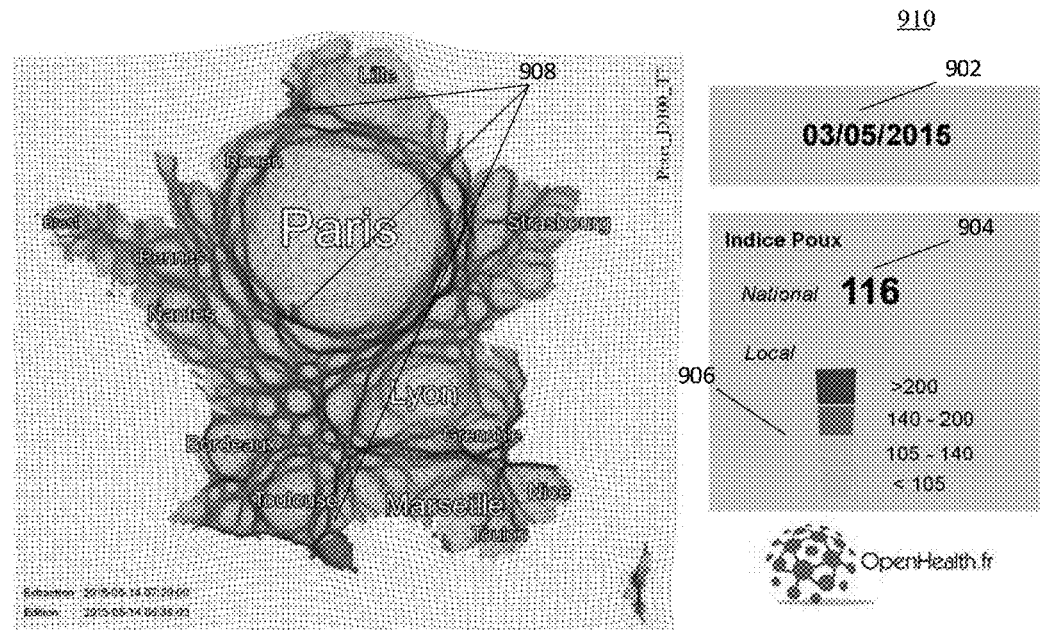
Figure 9C:
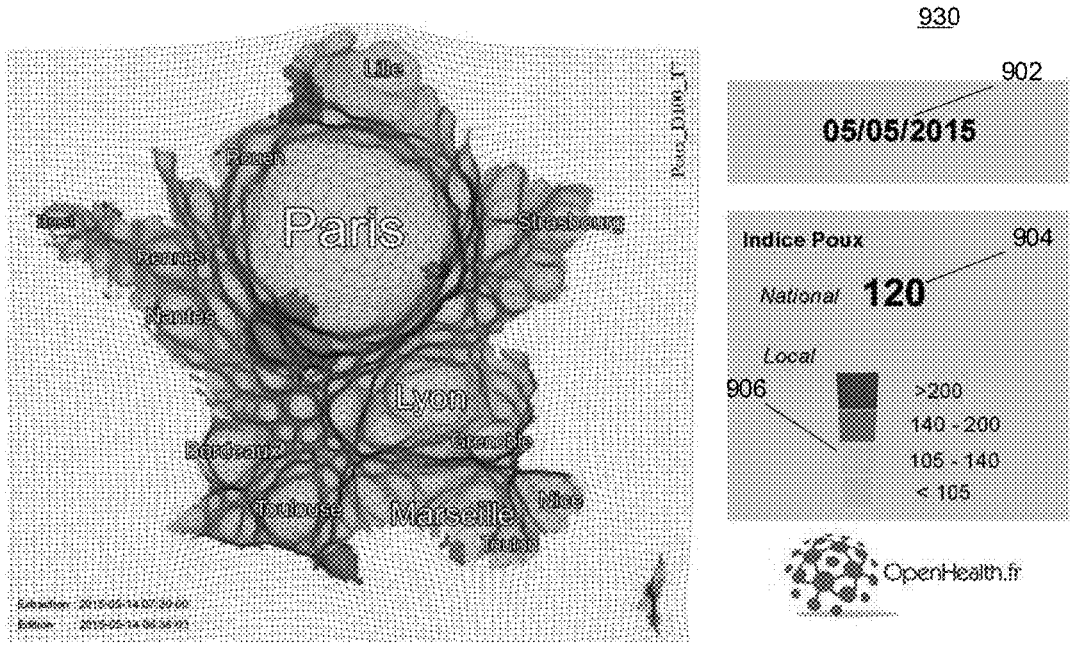
Figure 9D:
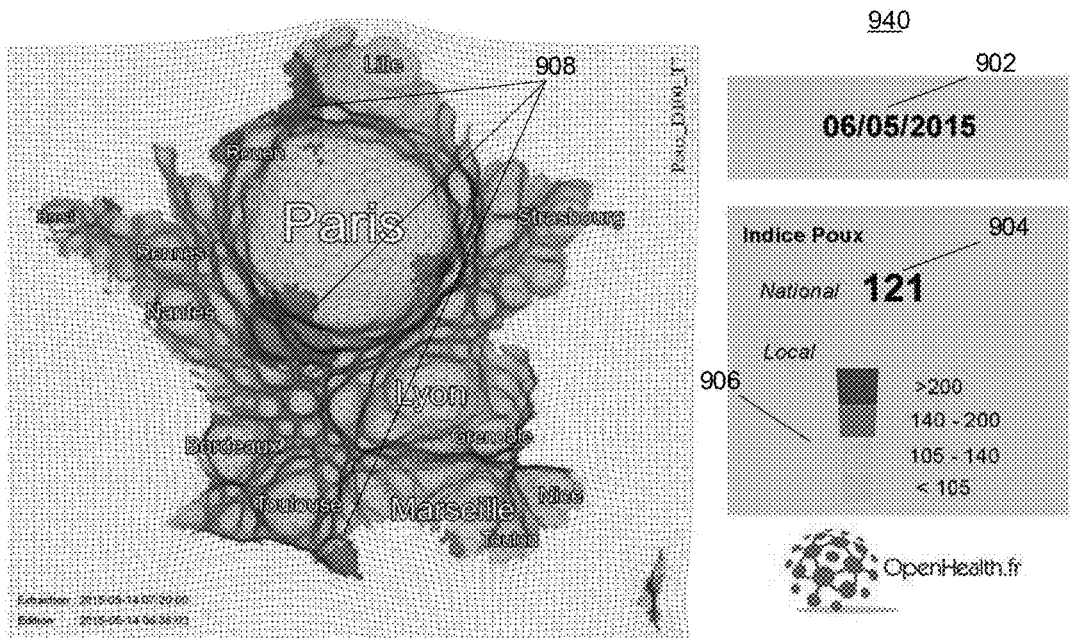

FIG. 8 illustrates a diagram of an exemplary environment 800 including a hardware server 820 in which the functionalities as discussed herein may be implemented. The hardware server 820 may include a processor as well as a memory 828. The memory 828 may store an operating system capable of facilitating the functionalities as described herein, as well as a database client, database server, web server, communications interfaces, and other software. The hardware server 820 may also store a set of applications (i.e., machine readable instructions). For example, one of the set of applications may be a machine learning algorithm configured to manage and organize access to Euclidean maps, cartograms, health or epidemiological data, shading scales, and other applications.

The processor may interface with the memory 828 to execute the operating system and the set of applications. The machine learning algorithm may access geographical collection unit database 802 and map database 804 to manage, organize, render, and edit cartograms. The memory 828 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others.

The hardware server 820 may further include a communication module configured to communicate data via one or more networks 822. According to some embodiments, the communication module can include one or more transceivers (e.g., WWAN, WLAN, and/or WPAN transceivers) functioning in accordance with IEEE standards, 3GPP standards, or other standards, and configured to receive and transmit data via one or more external ports. For example, the communication module may send, via the network 822, a stack of chronological health indication cartograms for rendering and interaction with a user 826 on client terminal 824. Client terminal 824 may include a user interface configured to present information to a user and/or receive inputs from the user. The user interface may include a display screen and I/O components (e.g., ports, capacitive or resistive touch sensitive input panels, keys, buttons, lights, LEDs, speakers, microphones, and others).

According to present embodiments, the user may access the hardware server 820 via the user interface of client terminal 824 to request cartograms, underlying cartogram data, cartogram metadata, cartogram availability data, and/ or other visualizations of the underlying data. In some embodiments, the hardware server 820 may perform the functionalities as discussed herein as part of a cloud network (not shown) or can otherwise communicate with other hardware or software components within the cloud to send, retrieve, or otherwise analyze, manipulate, process, store, or transmit data. The hardware server 828 may be a local or remote server. For instance, the hardware server 828 may be a remote server such as a cloud server. Additionally or alternatively, hardware server 828 may be located at the source of the underlying map data, and may utilize other servers located locally or remotely.

In general, a computer program product in accordance with an embodiment may include a computer usable storage medium (e.g., standard random access memory (RAM), an optical disc, a universal serial bus (USB) drive, or similar components) having computer-readable program code embodied therein, wherein the computer-readable program code is adapted to be executed by the process (e.g., working in connection with the operating system) to facilitate the functions as described herein. In this regard, the program code may be implemented in any desired language, and may be implemented as machine code, assembly code, byte code, interpretable source code or the like (e.g., via Python, or other languages, such as C, C++, Java, Actionscript, Objective-C, Javascript, CSS, XML). In some embodiments, the computer program product may be part of a cloud network of resources.

Hardware server 820 may be communicatively coupled to map database 804 and geographical collection unit database 802 to store various data needed to render health indication cartograms. Geographical collection unit database 802 may store sets of geographical collection units pertaining to any underlying data to be illustrated on a health indication cartogram. Geographical collection unit database 802 may receive as inputs health indication values 806, geographical locations 808, and/or collection date stamps 810 in connection with each stored geographical collection unit. Geographical collection units may originate from a variety of sources, including publicly available data, data generated in connection with commercial activity, government data, or data collected by hardware server 820. Map database 804 may receive as inputs geographical representation unit tessellations 812, pre-rendered contiguous demographically-based cartograms 814, Euclidean maps 816, and shaded health indication cartograms 818. In some embodiments, hardware server 820 may be further communicatively coupled to additional databases, either locally or remotely via network 822.

VIII. Exemplary Chronological Health Indication Cartograms

FIGS. 9A-9D are a stack of four chronological health indication cartograms 900, 910, 930, and 940 based on an isodemographic cartogram of France. The four cartograms are identified by date stamp 902, indicating the date of the epidemiological data presented to the viewer in the cartogram rendering. The cartograms may display shading scale 906 for indication of the shading scale, which may be a predetermined or procedurally determined scale. The cartograms may include summary data 904 such as a national index. The progression to cartogram 910 from cartogram 900 illustrates the emergence of local hotspots 908 and an increase in the national index reflected by summary data 904. Health indication cartograms 930 and 940 illustrate increasing local hotspots 908 wherein darker shaded geographical representation units comprise an increasing number of geographical representation units surrounding hotspots 908.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In exemplary embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise. This detailed description is to be construed as examples and does not describe every possible embodiment, as describing every possible embodiment would be impractical, if not impossible. One could implement numerous alternate embodiments, using either current technology or technology developed after the filing date of this application.

What is claimed is:

1. A method of rendering a health indication cartogram, comprising:
   receiving a health indication cartogram request from a user, the health indication cartogram request including a geographical area and a plurality of geographical collection units;
   retrieving, from a map database server, a geographic map projected in a Euclidean plane, the geographic map representing at least a portion of the geographical area;
   tessellating the geographic map projected in a Euclidean plane into a plurality of cartogram tiles;
   receiving demographic data associated with each of the plurality of cartogram tiles indicating a demographic characteristic of the geographic area represented by each cartogram tile;
   proportionally distorting the area of each of the plurality of cartogram tiles to form a demographically-based cartogram such that the borders of each cartogram tile remain contiguous to its neighboring cartogram tiles and the surface of each cartogram tile is proportional to the demographic characteristic of the geographic area represented by the cartogram tile;
   receiving, from a geographical collection unit database, data associated with each of a plurality of geographical collection units, each geographical collection unit comprising a health indicator value and a geographic location coordinate;
   tessellating the demographically-based cartogram into a plurality of geographical representation units, each geographical representation unit corresponding to a subset of the geographical area and each geographical representation unit having a health indicator value associated therewith, the health indicator value associated therewith being based on the data associated with ones of the plurality of geographical collection units located inside each geographical representation unit;
   geographically smoothing the health indicator value of each geographical representation unit according to a weighting function applied to each geographical collection unit located in the geographic area corresponding to the geographical representation unit,
   wherein the weighting function depends on a) a predetermined distance of interest; and b) the health indicator value of any other geographical collection units at a distance closer than the predetermined distance of interest, wherein the distance to any other geographical collection units is the distance as measured along the distorted surface of the demographically-based cartogram; and
   rendering a health indication cartogram to the user wherein each geographical representation unit is shaded according to a predetermined shading scale based on the geographically smoothed health indicator value of the geographical representation unit.

2. The method of claim 1, further comprising:
   wherein the demographic characteristic is one of total population, economic product, highest educational level attained, or age.

3. The method of claim 1, further comprising:
   wherein tessellating the geographic map projected in a Euclidean plane into a plurality of cartogram tiles comprises a regular tessellation.

4. The method of claim 1, further comprising:
   wherein tessellating the geographic map projected in a Euclidean plane into a plurality of cartogram tiles comprises a semi-regular tessellation.

5. The method of claim 1, further comprising:
   wherein each geographical collection unit further comprises a demographic value; and
   wherein the weighting function further depends on the geographical collection unit's demographic value.

6. The method of claim 1, further comprising:
   wherein the weighting function is a biweight function.

7. The method of claim 1, further comprising:
   wherein the weighting function is a Gaussian function.

8. The method of claim 1, further comprising:
   wherein tessellating the demographically-based cartogram into a plurality of geographical representation units comprises tessellating the demographically-based cartogram into hexagons.

9. The method of claim 1, further comprising:
   wherein the predetermined shading scale is a color scale.

10. The method of claim 1, further comprising:
    wherein the predetermined shading scale is a greyscale.

11. A computer device for rendering a health indication cartogram from demographic and health indicator data, the computer device comprising:

one or more processors; and one or more memories coupled to the one or more processors;

the one or more memories including computer executable instructions stored therein that, when executed by the one or more processors, cause the one or more processors to:

render to a user a contiguous demographically-based cartogram representing a geographic area based on a geographic map projected in a Euclidean plane retrieved from a map server;

wherein the demographically-based cartogram is tessellated into a plurality of cartogram tiles, and each cartogram tile is distorted to represent an equal value of a demographic characteristic associated with the geographic area represented by the cartogram tile;

wherein said demographically-based cartogram is further tessellated into geographical representation units;

wherein at least one geographical representation unit is associated with a plurality of geographical collection units, each geographical collection unit comprising a health indicator value and a geographic location and being retrieved from a geographical collection unit database;

wherein said geographical representation units are assigned health indicator values according to geographically smoothed health indicator values, the geographically smoothed health indicator values being based on a weighting function, wherein said weighting function depends on: a) a predetermined distance of interest; and b) the health indicator value of any geographical collection units at a distance less than the predetermined distance of interest, wherein the distance to any other geographical collection units is the distance as measured along the distorted surface of the demographically-based cartogram; and wherein said geographical representation units are shaded on a predetermined shading scale according to each geographical representation unit's geographically smoothed health indicator value.

12. The health indication cartogram of claim 11, further comprising:

wherein the demographic characteristic is the total number of residents.

13. The health indication cartogram of claim 11, further comprising:

wherein each geographical collection unit further comprises a demographic value; and wherein the geographically smoothed health indicator values further depend on the geographical collection unit's demographic value.

14. The health indication cartogram of claim 11, further comprising:

wherein the demographically-based cartogram is tessellated into hexagon-shaped geographical representation units.

15. The health indication cartogram of claim 11, further comprising:

wherein the cartogram tiles are in the shape of a hexagon.

16. The health indication cartogram of claim 11, further comprising:

wherein the predetermined shading scale is a color scale.

17. The health indication cartogram of claim 11, further comprising:

wherein the predetermined shading scale is a grey scale.

18. A health indication cartogram server, comprising:

a map database containing a plurality of contiguous demographically-based cartograms representing a geographical area;

wherein each demographically-based cartogram is tessellated into a plurality of cartogram tiles, each cartogram tile being distorted to represent equal total population, and each demographically-based cartogram further tessellated into a plurality of geographical representation units;

wherein each geographical representation unit has a health indicator value associated therewith;

a geographical collection unit database containing geographical collection units located in the geographical area, each geographical collection unit including a health indicator value, a geographical location, and a collection date stamp;

a communications interface;

one or more processors; and a program memory storing instructions that, when executed by the one or more processors, cause the one or more processors to:

retrieve a contiguous demographically-based cartogram representing a geographical area from the map database;

retrieve geographical collection units from the geographical collection unit database with collection date stamps within a predetermined range;

geographically smooth the health indicator values of each geographical representation unit according to a weighting function applied to each geographical collection unit located in the geographical representation unit, wherein the weighting function depends on a) a predetermined distance of interest; and b) the health indicator value of any geographical collection units at a distance closer than the predetermined distance of interest, wherein the distance to any other geographical collection units is the distance as measured along the distorted surface of the demographically-based cartogram;

shade each geographical representation unit according to a predetermined shading scale based on the geographically smoothed health indicator values of the geographical representation unit;

render a plurality of health indication cartograms, each containing only geographical representation units with collection date stamps within a predetermined range; and transmit the plurality of health indication cartograms to a client in response to a client request via the communications interface for display in chronological order according the collection date stamps.

19. The health indication cartogram server of claim 18, further comprising:

wherein each demographically-based cartogram is tessellated into a plurality of regular cartogram tiles.

20. The health indication cartogram server of claim 18, further comprising:

wherein each geographical collection unit further comprises a demographic value; and wherein the weighting function depends on the geographical collection unit's demographic value.

21. The health indication cartogram server of claim 18, further comprising:

wherein the weighting function is a biweight function.

22. The health indication cartogram server of claim 18, further comprising:

wherein the weighting function is a Gaussian function.

23. The health indication cartogram server of claim 18, further comprising:
   wherein the cartogram tiles are hexagons.

24. The health indication cartogram server of claim 18, further comprising:
   wherein the geographical representation units are hexagons.

25. The health indication cartogram server of claim 18, further comprising:
   wherein the date stamp further includes a time stamp.

26. The health indication cartogram server of claim 18, further comprising:
   wherein the predetermined distance of interest for the weighting function can be varied such that the geographical representation units form different numbers of distinct contiguous shading zones.

27. The health indication cartogram server of claim 18, further comprising:
   wherein the predetermined shading scale is a color scale.

28. The health indication cartogram server of claim 18, further comprising:
   wherein the predetermined shading scale is a grey scale.

29. The health indication cartogram server of claim 18, further comprising:
   wherein the predetermined range of date stamps comprises only date stamps from a single day.

* * * * *